United States Patent [19]
Aulbach et al.

[11] Patent Number: 5,962,359
[45] Date of Patent: Oct. 5, 1999

[54] METALLOCENE COMPOUND AND ITS USE AS CATALYST COMPONENT

[75] Inventors: Michael Aulbach, Hofheim; Cornelia Fritze, Frankfurt; Hans-Friedrich Herrmann, Dornheim; Frank Küber, Oberursel; Walter Spaleck, Liederbach; Roland Zenk, Kelkheim, all of Germany

[73] Assignee: Targor GmbH, Germany

[21] Appl. No.: 08/577,799

[22] Filed: Dec. 22, 1995

[30] Foreign Application Priority Data

Dec. 28, 1994 [DE] Germany .............................. 44 46 922

[51] Int. Cl.$^6$ .......................... C08F 4/642; C07F 17/00; C07F 7/28

[52] U.S. Cl. .......................... 502/103; 502/104; 502/117; 502/120; 502/132; 526/160; 526/943; 556/11; 556/53

[58] Field of Search .................................. 502/103, 117, 502/104, 120, 132; 556/11, 53, 160, 943; 526/160, 943

[56] References Cited

U.S. PATENT DOCUMENTS

| | | | |
|---|---|---|---|
| 5,324,800 | 6/1994 | Welborn, Jr. et al. | 526/160 |
| 5,359,102 | 10/1994 | Inoue et al. | 556/53 |
| 5,372,980 | 12/1994 | Davis | 502/103 |

FOREIGN PATENT DOCUMENTS

| | | |
|---|---|---|
| 2017190 | 11/1990 | Canada . |
| 2095100 | 10/1993 | Canada . |
| 0 129 368 B1 | 12/1984 | European Pat. Off. . |
| 0 399 348 A2 | 11/1990 | European Pat. Off. . |
| 0 528 041 A1 | 2/1993 | European Pat. Off. . |
| 0 578 838 A1 | 1/1994 | European Pat. Off. . |
| 0 632 063 A1 | 1/1995 | European Pat. Off. . |

OTHER PUBLICATIONS

Aulbach et al., "Metallocene—maβgeschneiderte Werkzeuge zur Herstellung von Polyolefinen", Chemie in unserer Zeit, 28. Jahry. 1994, Nr. 4.

Möhring et al., "Homogeneous Group 4 metallocene Ziegler–Natta catalysts: the influence of cyclopentadienyl–ring substituents", Journal of Organometallic Chemistry, 479 (1994), 1–29.

Diamond et al., "Synthesis of Homo–and Hetero–bimetallic Complexes incorporating the [($\eta^5$–$C_5H_4$)$CMe_2$($\eta^5$–$C_9H_6$)] Ligand", J. Chem. Soc., Chem. Commun., 1994, 727–728.

Amorose et al., "1—Sila–3–metallacyclobutanes, Precursors for the Generation of Highly Electrophilic Group 4 Metallocene Alkyl Cations. Spectroscopic and Structural Evidence of a Weakly Bound THF Ligand in [($C_5Me_5$)$_2$Zr($CH_2SiMe_3$)(THF)][$BPh_4$]", Organometallics 1991, 10, 2191–2198.

Reddy et al., "Synthesis and Characterization of Binuclear Zirconocene Complexes Linked by a Bridged Bis(cyclopentadienyl) Ligand", Organometallics 1989, 8, 2107–2113.

Reddy et al., "Synthesis and Characterization of Binuclear Zirconocenophane Hydrides. The Molecular Structure of [$SiMe_2$($C_5H_4$)$_2$][($\eta^5$–$C_5H_5$)ZrCl($\mu$–H)]$_2$", Organometallics 1989, 8, 547–549.

Kabi–Satpathy et al., "Synthesis and structural characterization of group 4 ansa–metallocene complexes containing a 1–sila–3–metallacyclobutane ring", Journal of Organometallic Chemistry, 364 (1989) 105–117.

*Primary Examiner*—Porfirio Nazario-Gonzalez
*Attorney, Agent, or Firm*—Connolly and Hutz

[57] ABSTRACT

The present invention relates to a multinuclear metallocene compound of the formula I,

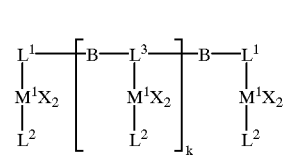

(I)

where $M^1$ is a tetravalent metal, $L^1$ are, independently of one another, identical or different and are each a substituted cyclopentadienyl group, $L^2$ and $L^3$ are, independently of one another, identical or different and are each a π ligand, B are, independently of one another, identical or different and are each a divalent bridging unit, X are, independently of one another, identical or different and are each a hydrogen atom, a halogen atom, a $C_1$–$C_{10}$-fluorocarbon radical or a hydrocarbon-containing radical having 1–40 carbon atoms, and k is an integer from 0 to 10. The metallocene compound of the present invention is suitable as a catalyst component for preparing olefin polymers.

10 Claims, No Drawings

METALLOCENE COMPOUND AND ITS USE AS CATALYST COMPONENT

The present invention relates to a new metallocene compound which is suitable as a catalyst component for olefin polymerization. The invention also relates to a process for preparing this metallocene compound. The invention further relates to a process for preparing polyolefins using the metallocene compound of the present invention.

Metallocene compounds of transition group IV are suitable, in the presence of methylaluminoxane (MAO), for the polymerization of olefins. The literature describes examples of bridged and unbridged metallocene compounds which, in combination with aluminoxanes or other cocatalysts, represent catalyst systems having sometimes very high activity and stereospecificity (Chem. unserer Zeit (1994) 28, 197; J. Organomet. Chem. (1994) 479, 1). Metallocene-catalysts are increasingly used for the copolymerization and terpolymerization of linear and cyclic olefins and also diolefins (EP 399 348).

Mononuclear metallocene dichloride complexes in the presence of MAO are suitable for the polymerization of ethylene and propylene (EP 129 368).

Also known are binuclear ansa-metallocene dichloride complexes in which the bridge atoms are part of a hydrocarbon ring system and which complexes are suitable, in the presence of MAO, for the syndiospecific polymerization of 1-olefins (EP 528 041). EP 632 063 also discloses binuclear metallocenes.

The only known examples of unbridged binuclear metallocene dichloride complexes with metals of transition group IV are those which contain as connecting element a divalent hydrocarbon radical or a dimethylsilyl group (J. Chem. Soc., Chem. Comm. (1994) 727; Organometallics (1991) 10, 2191; Organometallics (1989) 8, 2107; Organometallics (1989) 8, 547; J. Organomet. Chem. (1989) 264, 105).

A disadvantage of the use of soluble (homogeneous) metallocene-methylaluminoxane catalyst systems in processes where the polymer formed is obtained as a solid is the formation of heavy deposits on reactor walls and stirrer. These deposits are formed by agglomeration of the polymer particles if the metallocene or aluminoxane or both are present in dissolved form in the suspension medium. Such deposits in the reactors have to be removed regularly, since these rapidly reach considerable thicknesses, have high strength and prevent heat exchange to the cooling medium.

To avoid reactor deposits, metallocenes can be supported. Processes for this purpose are known (EP 578 838). However, the dissolution of the supported catalyst from the particle surface (leaching) cannot yet be completely prevented.

It is an object of the present invention to find a metallocene compound which avoids the disadvantages of the prior art and, in particular, produces polyolefins such as polyethylene with high activity and high molecular weight. It is a further object to find a metallocene compound which as a result of multiple fixing to the support surface has a substantially more favorable leaching behavior.

The present invention accordingly provides a multinuclear metallocene compound of the formula I,

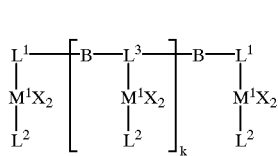

where $M^1$ is a tetravalent metal, $L^1$ are, independently of one another, identical or different and are each a substituted cyclopentadienyl group, $L^2$ and $L^3$ are, independently of one another, identical or different and are each a π ligand, B are, independently of one another, identical or different and are each a divalent bridging unit, X are, independently of one another, identical or different and are each a hydrogen atom, a halogen atom, a $C_1$–$C_{10}$-fluorocarbon radical or a hydrocarbon-containing radical having 1–40 carbon atoms, and k is an integer from 0 to 10.

$M^1$ are preferably identical and are each titanium, zirconium, hafnium, vanadium, niobium, tantalum, scandium, yttrium or a rare earth metal, particular preference being given to titanium or zirconium.

$L^1$ are identical or different, preferably identical, and are each a substituted cyclopentadienyl group.

$L^2$ are identical or different, preferably identical, and are preferably each a cyclopentadienyl group which is preferably substituted.

$L^3$ are identical or different, preferably identical, and are preferably each a cyclopentadienyl group which is preferably substituted.

For the purposes of the present invention, a cyclopentadienyl group is an unsubstituted or substituted cyclopentadienyl group, such as methylcyclopentadienyl, indenyl, 2-methylindenyl, 2-methyl-4-phenylindenyl, 2-ethyl-4-naphthylindenyl, 2-methyl-4,6-diisopropylindenyl, 4,5-benzoindenyl, 2-methyl-4,5-benzoindenyl, fluorenyl or 2,7-di-tert-butylfluorenyl.

The unsubstituted or substituted cyclopentadienyl groups can bond to one other atom ($L^2$), be substituted cyclopentadienylidene groups bonding to two other atoms ($L^1$) or be unsubstituted or substituted cyclopentadienylylidene groups bonding to three other atoms ($L^3$).

X are preferably identical and are each a hydrogen atom, a halogen atom, a $C_1$–$C_{10}$-fluorocarbon radical such as $CF_3$, or a hydrocarbon-containing radical having 1–40 carbon atoms such as $C_1$–$C_{20}$-alkyl, $C_6$–$C_{30}$-aryl, a radical $OR^1$ or $NR^1_2$, where $R^1$ are identical or different, and hydrogen, a $C_1$–$C_{30}$-hydrocarbon-containing radical such as $C_1$–$C_{20}$-alkyl, $C_6$–$C_{30}$-aryl or a halogenated $C_1$–$C_{20}$-hydrocarbon radical.

B is a divalent $C_1$–$C_{40}$-hydrocarbon-containing bridged unit and preferably has the formula II

where E are identical or different and are each a hetero atom (i.e. an atom which is not carbon or hydrogen), preferably E is an element of main group IV of the Periodic Table of the Elements with the exception of carbon, or is an element of main group V or VI of the Periodic Table of the Elements, particularly preferably silicon or germanium.

$R^2$ is a hydrocarbon-containing radical having from one to forty carbon atoms such as, for example, $C_1$–$C_{20}$-alkyl or $C_6$–$C_{30}$-aryl. The radicals $R^2$ can also be cyclically connected to one another. n is the valence of E minus 2, for example n is equal to 2 if E is an element of main group IV, n is preferably one if E is an element of main group V and n is zero if E is an element of main group VI. K is a bridging unit between the two hetero atoms E and is preferably a hydrocarbon-containing divalent radical having from one to forty carbon atoms, preferably 2 carbon atoms. m is one or, if the two elements E are directly connected to one another, zero.

k is an integer from 0 to 10, preferably 0, 1 or 2.

Examples of $L^1$ are:

methylcyclopentadienylidene, tert-butylcyclopentadienylidene, dimethylcyclopentadienylidene, 1H-inden-1-ylidene, 4-phenyl-1H-inden-1-ylidene, 4-naphthyl-1H-inden-1-ylidene, 2,4,7-trimethyl-1H-inden-1-ylidene, 2-methyl-1H-inden-1-ylidene, 2-methyl-4,6-diisopropyl-1H-inden-1-ylidene, 2-methyl-4-phenyl-1H-inden-1-ylidene, 2-methyl-4,5-benzo-1H-inden-1-ylidene, 4,5-benzo-1H-inden-1-ylidene, 9H-fluoren-9-ylidene, 2,7-dibromo-9H-fluoren-9-ylidene, 4,5-dimethyl-9H-fluoren-9-ylidene, 3-tert-butyl-9H-fluoren-9-ylidene, 7H-benzo[C]fluoren-7-ylidene.

Examples of $L^2$ are:

cyclopentadienyl, methylcyclopentadienyl, dimethylcyclopentadienyl, tert-butylcyclopentadienyl, pentamethylcyclopentadienyl, pentaethylcyclopentadienyl, pentaphenylcyclopentadienyl, indenyl, 1,2,3-trimethylindenyl, 9H-fluorenyl, 2,7-diphenyl-9H-fluorenyl, 9-trimethylsilyl-9H-fluorenyl, 4,5-dimethyl-9H-fluorenyl and 3-tert-butyl-9H-fluorenyl.

Examples of $L^3$ are:

cyclopentadien-1-yl-2,4-ylidene, 9H-fluoren-9-yl-2,7-ylidene, 1H-inden-1-yl-4,7-ylidene, 1H-inden-1-yl-3,7-ylidene.

Examples of multinuclear metallocene compounds of the formula I are:

[1,1,2,2-tetramethyl-1,2-bis(1H-indenyl-1-ylidene)-disilane]bis(cyclopentadienyltitanium dichloride)

[1,4-disila-1,4-bis(1H-indenyl-1-ylidene)-1,1,4,4-tetramethylbutane]bis(cyclopentadienyltitanium dichloride)

[1,5-disila-1,5-bis(1H-indenyl-1-ylidene)-1,1,5,5-tetramethylpentane]bis(cyclopentadienyltitanium dichloride)

[1,6-disila-1,6-bis(1H-indenyl-1-ylidene)-1,1,6,6-tetramethylahexane]bis(cyclopentadienyltitanium dichloride)

[1,8-disila-1,8-bis(1H-indenyl-1-ylidene)-1,1,8,8-tetramethyloctane]bis(cyclopentadienyltitanium dichloride)

[1,10-disila-1,10-bis(1H-indenyl-1-ylidene)-1,1,10,10-tetramethyldecane]bis(cyclopentadienylzirconium dichloride)

[1,12-disila-1,12-bis(1H-indenyl-1-ylidene)-1,1,12,12-tetramethyldodecane]bis(cyclopentadienyl-zirconium dichloride)

[1,4-disila-1,4-bis(1H-indenyl-1-ylidene)-1,1,4,4-tetramethyl-2-butyne]bis(cyclopentadienylzirconium dichloride)

1,4-bis[dimethyl(1H-indenyl-1-ylidene)silyl]benzenebis-(cyclopentadienylzirconium dichloride)

1,4-bis[2-[dimethyl-(1H-indenyl-1-ylidene)silyl]bis-(cyclopentadienylzirconium dichloride)

[1,1,2,2-tetramethyl-1,2-bis(9H-fluorenyl-9-ylidene) disilane]bis(cyclopentadienylzirconium dichloride)

[1,4-disila-1,4-bis(9H-fluorenyl-9-ylidene)-1,1,4,4-tetramethylbutane]bis(cyclopentadienylzirconium dichloride)

[1,5-disila-1,5-bis(9H-fluorenyl-9-ylidene) 1,1,5,5-tetramethylpentane]bis(cyclopentadienylzirconium dichloride)

[1,6-disila-1,6-bis(9H-fluorenyl-9-ylidene)-1,1,6,6-tetramethylhexane]bis(cyclopentadienylzirconium dichloride)

[1,8-disila-1,8-bis(9H-fluorenyl-9-ylidene)-1,1,8,8-tetramethyloctane]bis(cyclopentadienylzirconium dichloride)

[1,10-disila-1,10-bis(9H-fluorenyl-9-ylidene)-1,1,10,10-tetramethyldecane]bis(cyclopentadienylhafnium dichloride)

[1,12-disila-1,12-bis(9H-fluorenyl-9-ylidene)-1,1,12,12-tetramethyldodecane]bis(cyclopentadienylhafnium dichloride)

[1,4-disila-1,4-bis-(9H-fluorenyl-9-ylidene)-1,1,4,4-tetramethyl-2-butyne]bis(cyclopentadienylhafnium dichloride)

1,4-bis[dimethyl(9H-fluorenyl-9-ylidene) silyl]benzene bis(cyclopentadienylhafniumdichloride)

1,4-bis [2-[dimethyl-(9H-fluorenyl-9-ylidene)silyl] ethyl]-bis(cyclopentadienylhafnium dichloride)

[1,1,2,2-tetramethyl-1,2-bis(1H-indenyl-1-ylidene)-disilane]bis(pentamethylcyclopentadienyltitanium dichloride)

[1,4-disila-1,4-bis 1H-indenyl-1-ylidene)-1,1,4,4-tetraethylbutane]bis(pentamethylcyclopentadienyltitanium dichloride)

[1,5-disila-1,5-bis(1H-indenyl-1-ylidene)-1,1,5,5-tetramethylpentane]bis (pentamethylcyclopentadienyltitanium dichloride)

[1,6-disila-1,6-bis(1H-indenyl-1-ylidene)-1,1,6,6-tetramethylhexane]bis (pentamethylcyclopentadienylzirconium dichloride)

[1,8-disila-1,8-bis 1H-indenyl-1-ylidene)-1,1,8,8-tetramethyloctane]bis (pentamethylcyclopentadienylzirconium dichloride)

[1,10-disila-1,10-bis(1H-indenyl-1-ylidene)-1,1,10,10-tetramethyldecane]bis (pentamethylcyclopentadienylzirconium dichloride)

[1,12-disila-1,12-bis(1H-indenyl-1-ylidene)-1,1,12,12-tetramethyldodecane]bis(pentamethylcyclopenta dienylzirconium dichloride)

[1,4-disila-1,4-bis(1H-indenyl-1-ylidene)-1,1,4,4-tetramethyl-2-butyne]bis (pentamethylcyclopentadienylhafnium dichloride)

1,4-bis[dimethyl(1H-indenyl-1-ylidene)silyl]benzenebis-(pentamethylcyclopentadienylhafnium dichloride)

1,4-bis[2-[dimethyl(1H-indenyl-1-ylidene) silyl]ethyl] bis-(pentamethylcyclopentadienylhafnium dichloride)

[1,1,2,2-tetramethyl-1,2-bis(9H-fluorenyl-9-ylidene)-disilane]bis(pentamethylcyclopentadienylzirconium dichloride)

[1,4-disila-1,4-bis(9H-fluorenyl-9-ylidene)-1,1,4,4-tetramethylbutane]bis (pentamethylcyclopentadienylzirconium dichloride)

[1,5-disila-1,5-bis(9H-fluorenyl-9-ylidene)-1,1,5,5-tetramethylpentane]bis (pentamethylcyclopentadienylhafnium dichloride)

[1,6-disila-1,6-bis(9H-fluorenyl-9-ylidene)-1,1,6,6-tetramethylhexane]bis (pentamethylcyclopentadienylhafnium dichloride)

[1,8-disila-1,8-bis(9H-fluorenyl-9-ylidene)-1,1,8,8-tetramethyloctane]bis (pentamethylcyclopentadienylhafnium dichloride)

[1,10-disila-1,10-bis(9H-fluorenyl-9-ylidene)1,1,10,10-tetramethyldecane]bis (pentamethylcyclopentadienyltitanium dichloride)

[1,12-disila-1,12-bis(9H-fluorenyl-9-ylidene)-1,1,12,12-tetramethyldodecane]bis(pentamethylcyclopentadienyltitanium dichloride)

[1,4-disila-1,4-bis(9H-fluorenyl-9-ylidene)-1,1,4,4-tetramethyl-2-butyne]bis(pentamethylcyclopentadienyltitanium dichloride)

1,4-bis[dimethyl(9H-fluorenyl-9-ylidene)silyl]benzenebis-(pentamethylcyclopentadienylzirconium dichloride)

1,4-bis[2-[dimethyl(9H-fluorenyl-9-ylidene)silyl]ethyl]-bis(pentamethylcyclopentadienylzirconium dichloride)

[1,4-disila-1,4-bis(3-tert-butyl-2,4-cyclopentadien-1-ylidene)-1,1,4,4-tetramethylbutane]bis(indenyldimethyltitanium)

[1,5-disila-1,5-bis(1H-indenyl-1-ylidene)-1,1,5,5-tetramethylpentane]bis(indenyldimethyltitanium)

[1,6-disila-1,6-bis(4,7-dimethyl-1-indenyl-1-ylidene)-1,1,6,6-tetramethylhexane]bis(indenyldimethylzirconium)

[1,8-disila-1,8-bis(2-ethyl-4-phenyl-1H-indenyl-1-ylidene)-1,1,8,8-tetramethyloctane]bis(indenylzirconium dichloride)

[1,10-disila-1,10-bis(2,7-dimethyl-9H-fluoren-9-ylidene)-1,1,10,10-tetramethyldecane]bis(cyclopentadienylzirconium dichloride)

[1,12-disila-1,12-bis(2,4-dimethyl-2,4-cyclopentadien-1-ylidene)-1,1,12,12-tetramethyldodecane]bis(cyclopentadienylzirconium dichloride)

[1,4-disila-1,4-bis(4,5-dimethyl-9H-fluoren-9-ylidene)-1,1,4,4-tetramethyl-2-butyne]bis(pentamethylcyclopentadienyldimethylzirconium)

1,4-bis[dimethyl(2,7-di-tert-butyl-9H-fluorenyl-9-ylidene)silyl]benzenebis(cyclopentadienylzirconium dichloride)

1,4-bis[2-[dimethyl(4-naphthyl-1H-indenyl-1-ylidene)-silyl]ethyl]bis(cyclopentadienyldimethylhafnium)

[1,8-disila-1,8-bis(2-methyl-1H-indenyl-1-ylidene)-1,1,8,8-tetraethyloctane)]bis[(2-methyl-4-phenyl-1H-indenyl)zirconium dichloride]

[1,6-disila-1,6-bis(4,5-benzo-1H-indenyl-1-ylidene)-1,1,6,6-tetraethoxyoctane)]bis[(2-methyl-4-naphthyl-1H-indenyl)zirconium dichloride]

[1,8-disila-1,8-bis(2,3-dimethyl-1H-indenyl-1-ylidene)-1,1,8,8-tetraethyl-3,4-dibutyl-3-octene) ]bis[(2-methyl-4,7-diisopropyl-1H-indenyl)zirconium dichloride]

[1,7-distanna-4-oxa-1,7-bis(tetramethylcyclopenta-2,4-dienyl-1-ylidene) -1,1-dimethyl-7,7-dibutylheptane]-bis[(2,7-dimethyl-9H-fluorenyl)zirconium dichloride]

[1,8-disila-1,8-bis(3-methylcyclopenta-2,4-dien-1-ylidene)-1,1,8,8-tetramethyloctane)]bis[(4-phenyl-1H-indenyl)zirconium dichloride]

The methods of preparing the ligand systems of the metallocene compound of the present invention are known in principle (Angew. Chem. (1989) 101, 1536).

The present invention further provides a process for preparing a metallocene compound of the formula I. In this process, a ligand precursor of the formula III is deprotonated (k+2) times by means of a suitable reagent of the formula IV $M^2R^3$ and reacted with a compound of the formula V to give a compound of the formula VI.

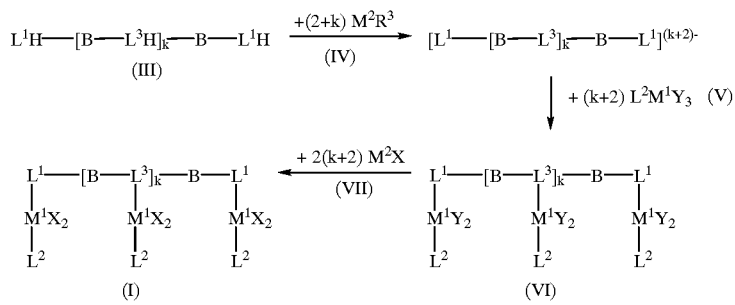

In the formula III, $L^1$, B and k are as defined for formula I. In formula IV, $M^2$ is an alkali metal such as lithium, sodium or potassium and $R^3$ is a hydrocarbon-containing radical having from 1 to 16 carbon atoms or is hydrogen. Methods of preparing compounds of the formula $L^2M^1Y_3$ (V) are known (Chem. Ber. (1994) 127, 3; Macromolecules (1993) 26, 5822; J. Organomet. Chem. (1988) 340, 37; Inorg. Chem. (1982) 21, 1277). In formula V, Y is a halogen atom, particularly chlorine, $L^2$ and $M^1$ are as defined for formula I. In formula VII, $M^2$ is an alkali metal such as lithium, sodium or potassium and X is as defined for formula I.

The reaction is preferably carried out in an aprotic solvent, e.g. toluene, hexane, diethyl ether or tetrahydrofuran. The temperature can be between −78 and 140° C., preferably from 0 to 110° C. The compound VI can be used in excess; preference is given to using from 2 to 3 equivalents of the compound VI based on the ligand precursor III.

The present invention also provides a process for preparing an olefin polymer by polymerization of at least one olefin in the presence of a catalyst comprising at least one metallocene compound and at least one cocatalyst, wherein the metallocene is a compound of the formula I.

Preference is given to homopolymerizing or copolymerizing olefins of the formula $R^a$—RH=CH—$R^b$, where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinylnorbornene. In the process of the present invention, preference is given to homopolymerizing ethylene, or copolymerizing ethylene with one or more 1-olefins having from 3 to 20 carbon atoms, for example propylene, and/or one or more dienes having from 4 to 20 carbon atoms, for example 1,4-butadiene. Examples of such copolymers are ethylene/propylene copolymers and ethylene/propylene/1,4-hexadiene copolymers.

The polymerization is preferably carried out at a temperature of from −60 to 300° C., particularly preferably from 50 to 200° C. The pressure is preferably from 0.5 to 64 bar.

The polymerization can be carried out in solution, in bulk, in suspension or in the gas phase, continuously or batchwise, and in one or more stages. A preferred embodiment is gas-phase polymerization.

The catalyst used in the process of the present invention preferably contains a metallocene compound of the formula I. It is also possible to use mixtures of two or more metallocene compounds of the formula I, or mixtures of metallocene compounds of the formula I with other bridged or unbridged metallocenes, e.g. for preparing polyolefins having a broad or multimodal molecular weight distribution.

In principle, a cocatalyst suitable for the process of the present invention can be any compound which, owing to its Lewis acidity, can convert the neutral metallocene into a cation and stabilize this ("labile coordination"). Furthermore, the cocatalyst or the anion formed therefrom should undergo no further reactions with the metallocene cation formed (EP 427 697). The cocatalyst used is preferably an aluminum compound and/or a boron compound.

The boron compound preferably has the formula $R^3NH_{4-x}BR^4{}_4$, $R^3{}_xPH_{4-x}BR^4{}_4$, $R^3{}_3CBR^4{}_4$ or $BR^4{}_3$, where x is a number from 1 to 4, preferably 3, the radicals $R^3$ are identical or different, preferably identical, and are $C_1$–$C_{10}$-alkyl or $C_6$–$C_{18}$-aryl radicals, or two radicals $R^3$ together with the atoms connecting them form a ring, and the radicals $R^4$ are identical or different, preferably identical, and are $C_6$–$C_{18}$-aryl which may be substituted by alkyl, haloalkyl or fluorine. In particular, $R^3$ is ethyl, propyl, butyl or phenyl and $R^4$ is phenyl, pentafluorophenyl, 3,5-bistrifluoromethylphenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula VIIIa for the linear type and/or the formula VIIIb for the cyclic type,

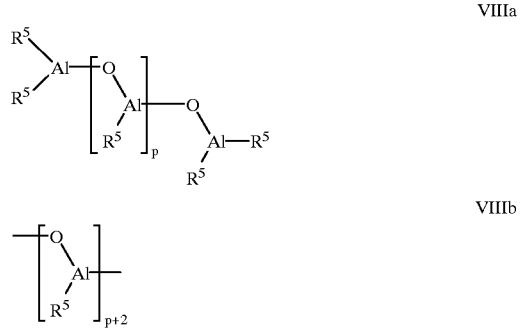

where, in the formulae VIIIa and VIIIb, the radicals $R^5$ are identical or different and are each hydrogen or a $C_1$–$C_{18}$-alkyl group or a $C_6$–$C_{18}$-aryl group or benzyl, and p is an integer from 2 to 50, preferably from 10 to 35.

The radicals $R^5$ are preferably identical and are each hydrogen, methyl, isobutyl, phenyl or benzyl, particularly preferably methyl.

The methods of preparing the aluminoxanes are known (DE 4 004 477).

The exact spatial structure of the aluminoxanes is not known (J. Am. Chem. Soc, 115 (1993) 4971). For example, it is conceivable that chains and rings join to form larger two- or three-dimensional structures.

Regardless of the manner of the preparation, all aluminoxane solutions have in common a variable content of unreacted aluminum starting compound which is present in free form or as adduct.

It is possible to preactivate the metallocene compound of the present invention prior to use in the polymerization by means of a cocatalyst, in particular an aluminoxane. This significantly increases the polymerization activity. The preactivation of the metallocene compound is preferably carried out in solution. Here, the metallocene compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of from $10^{-4}$ to 1 mol per mol of aluminum. The preactivation time is from 5 minutes to 60 hours, preferably from 5 to 60 minutes. The preactivation is carried out at a temperature of from −78 to 100° C., preferably from 0 to 70° C.

The metallocene compound is here preferably used in a concentration, based on the transition metal, of from $10^{-3}$ to $10^{-8}$, preferably from $10^{-4}$ to $10^{-7}$, mol of transition metal per $dm^3$ of solvent or per $dm^3$ of reactor volume. The aluminoxane is preferably used in a concentration of from $10^{-6}$ to $\mathbf{10^{-1}}$ mol, preferably from $10^{-5}$ to $10^{-2}$ mol, per $dm^3$ of solvent or per $dm^3$ of reactor volume. The other cocatalysts mentioned are used in approximately equimolar amounts to the metallocene compound. In principle, however, higher concentrations are also possible.

To remove catalyst poisons present in the olefin, purification using an aluminum compound, preferably an aluminum alkyl such as trimethylaluminum or triethylaluminum, is advantageous. This purification can be carried out either in the polymerization system itself or the olefin is, prior to addition to the polymerization system, brought into contact with the aluminum compound and subsequently separated off again.

In the process of the present invention, hydrogen can be added as molecular weight regulator and/or to increase the activity. This enables low molecular weight polyolefins such as waxes to be obtained.

In the process of the present invention, the metallocene compound is preferably reacted with the cocatalyst outside the polymerization reactor in a separate step using a suitable solvent. the catalyst can be applied to a support during this procedure.

In the process of the present invention, a prepolymerization can be carried out by means of the metallocene compound. The prepolymerization is preferably carried out using the (or one of the) olefin(s) used in the polymerization.

The catalyst used in the process of the present invention can be supported. The application to a support allows, for example, the particle morphology of the polyolefin prepared to be controlled. Here, the metallocene compound can first be reacted with the support and subsequently with the cocatalyst. The cocatalyst can also be supported first and subsequently reacted with the metallocene compound. It is also possible to support the reaction product of metallocene compound and cocatalyst. Suitable support materials are, for example, silica gels, aluminum oxides, solid aluminoxane or other inorganic support materials such as, for example, magnesium chloride. Another suitable support material is a polyolefin powder in finely divided form. The preparation of the supported cocatalyst can, for example, be carried out as described in EP 567 952.

If the polymerization is carried out as a suspension or solution polymerization, an inert solvent customary for the Ziegler low-pressure process is used. For example, the polymerization is carried out in an aliphatic or cycloaliphatic hydrocarbon; examples which may be mentioned of such hydrocarbons are propane, butane, hexane, heptane, isooctane, cyclohexane and methylcyclohexane. It is also possible to use a petroleum fraction or hydrogenated diesel oil fraction. Toluene can also be used. The polymerization is preferably carried out in the liquid monomer.

If inert solvents are used, the monomers are metered in in gaseous or liquid form.

The polymerization time can be any desired, since the catalyst system to be used in the process of the present invention has only a slight time-dependent fall in the polymerization activity.

The polymers prepared by the process of the present invention are suitable, in particular, for producing shaped bodies such as films, plates or large hollow bodies (e.g. pipes).

The metallocene compound of the present invention can advantageously be used for preparing copolymers, in particular ethylene-containing copolymers, having a low density, for example LLDPE. In particular, the metallocene compound of the present invention is suitable for preparing copolymers, in particular ethylene-containing copolymers, having a low density using low comonomer concentrations. This is advantageous, in particular, when a low comonomer concentration is to be maintained out of technical or economic considerations, e.g. when, in the gas-phase polymerization, comonomers condense and cause technical difficulties when the saturation concentration is exceeded. Particularly advantageous is the use of the metallocene compound of the present invention in the copolymerization with relatively high-boiling comonomers in the gas-phase polymerization.

EXAMPLES

Preparation and handling of organometallic compounds were carried out with exclusion of air and moisture under protective argon gas (Schlenk technique). All solvents required were, prior to use, dried by boiling for a number of hours over suitable desiccants and subsequent distillation under argon.

The compounds were characterized by means of $^1$H—NMR spectroscopy.

Example 1

[1,4-Disila-1,4-bis(9H-fluorenyl-9-ylidene)-1,1,4,4-tetramethylbutane]bis(cyclopentadienylzirconium dichloride) (1):

5.0 g (10.5 mmol) of 1,1,4,4-tetramethyl-1,4-difluorenyl-1,4 -disilabutane are suspended in 100 ml of diethyl ether and reacted with 13.0 ml (21 mmol) of n-butyllithium (1.6 mol in hexane). The yellow suspension is stirred for 8 hours at room temperature and subsequently cooled to 0° C. 5.5 g (21 mmol) of cyclopentadienylzirconium trichloride are then added, and the mixture is stirred for 30 minutes at 0° C. and one hour at room temperature. The orange suspension is feed of solvent under reduced pressure, the residue is extracted with methylene chloride and filtered through a glass frit. At −30° C., a total of 4.25 g (4.6 mmol, 44%) of the binuclear complex 1 crystallize out in the form of yellow crystals.

$^1$H—NMR (300 MHz, CDCl$_3$, 25° C., δ (ppm) rel. CH$_2$Cl$_2$): 8.14–8.08 (m, 4 H, C$_{13}$H$_8$), 7.77–7.68 (m, 4 H, C$_{13}$H$_8$), 7.47–7.40 (m, 8 H, C$_{13}$H$_8$), 5.73 (s, 10 H, C$_5$H$_5$), 0.77 (s, 4 H, CH$_2$CH$_2$), 0.59 (s, 12 H, Si(CH$_3$)$_2$).

Example 2

(1,4-Disila-1,4-bis(1H-indenyl-1-ylidene)-1,1,4,4-tetramethylbutane]bis(cyclopentadienylzirconium dichloride) (2):

4.0 g (10.7 mmol) of 1,1,4,4-tetramethyl-1,4-diindenyl-1,4-disilabutane are dissolved in 80 ml of diethyl ether and reacted with 13.5 ml (21.4 mmol) of n-butyllithium (1.6 molar in hexane). The yellow solution is stirred for 4 hours at room temperature and is subsequently admixed with 5.65 g (21.6 mmol) of cyclopentadienylzirconium trichloride. Within minutes, a red, at first oily suspension is formed, and this changes into a yellow suspension over a period of 3 hours. The solvent is removed via a glass frit, the residue is washed with 50 ml of diethyl ether and dried in vacuo. The residue is extracted with methylene chloride, filtered through a glass frit and crystallized at −30° C. The yield of finely crystalline 2 is 2.8 g (3.4 mmol, 32%).

$^1$H—NMR (300 MHz, CDCl$_3$, 25° C., δ (ppm) rel. CH$_2$Cl$_2$): 7.76–7.66 (m, 4 H, C$_9$H$_6$), 7.38–7.26 (m, 4 H, C$_9$H$_6$), 6.98 (d, 2 H, C$_9$H$_6$), 6.84 (d, 2 H, C$_9$H$_6$), 6.05 (s, 10 H, C$_5$H$_5$), 0.72 (m, 4 H, CH$_2$CH$_2$), 0.46 (S, 6 H, SiCH$_3$), 0.40 (s, 6 H, SiCH$_3$).

Example 3

[1,4-Disila-1,4-bis(1H-indenyl-1-ylidene)-1,1,4,4-tetramethylbutane]bis (pentamethylcyclopentadienylzirconium dichloride) (3):

6.0 g (16.0 mmol) of 1,1,4,4-tetramethyl-1,4-diindenyl-1,4-disilabutane are dissolved in 250 ml of diethyl ether and reacted with 20.0 ml (31.0 mmol) of n-butyllithium (1.6 molar in hexane). The pale yellow solution is stirred for 8 hours at room temperature and is subsequently admixed with 10.3 g (31.0 mmol) of pentamethylcyclopentadienylzirconium trichloride. Within minutes, a yellow suspension forms and this is stirred for a further three hours at room temperature. The lithium chloride is removed via a glass frit and the residue is washed with 200 ml of diethyl ether. The combined ether solutions are evaporated to 150 ml and crystallized at −20° C. The yield of 3 is 4.5 g (4.7 mmol, 29%).

$^1$H—NMR (300 MHz, CDCl$_3$, 25° C., δ (ppm) rel. CHCl$_3$: 7.92 (m, 2 H, C$_9$H$_6$), 7.65 (m, 2 H, C$_9$H$_6$), 7.44 (m, 4 H, C$_9$H$_6$), 6.46 (s, 4 H, C$_9$H$_6$), 2.18 (s, 30 H, C$_5$Me$_5$), 0.82 (m, 4 H, CH$_2$CH$_2$), 0.58 (s, 6 H, SiCH$_3$), 0.52 (s, 6 H, SiCH$_3$).

Polymerization Example 1

0.20 mg of the metallocene from Example 1 were dissolved in 1.25 ml of MAO solution in toluene and stirred for 15 minutes. In parallel thereto, a 1.5 dm$^3$ stirred reactor which has been made inert is charged with 750 ml of diesel oil (boiling point: 100 to 120° C.) and 3.75 ml of MAO solution in toluene, and is heated to 70° C. The catalyst solution is added and polymerization is carried out for 1 hour at 750 rpm using 7 bar of ethylene. The reactor is subsequently vented, the polymer is filtered from the suspension, washed with acetone and dried for 12 hours in a vacuum drying oven. This gives 14 g of polyethylene having an VN of 711 ml/g.

Polymerization Example 2

Polymerization was carried out using the procedure of Polymerization Example 1, but using 0.6 mg of the metallocene from Example 2.

This gives 29.4 g of polyethylene having a VN of 874 ml/g. GPC analysis indicates $M_w$=551,000 g/mol and $M_w/M_n$=5.2.

Polymerization Example 3

Using 0.5 mg of the metallocene from Example 2, polymerization was carried out by a method similar to Polymerization Example 2, with 0.5 bar of hydrogen being charged first and then supplemented with ethylene to 7 bar. This gives 42.3 g of polyethylene having a VN of 113 ml/g.

Polymerization Example 4

Polymerization was carried out using the procedure of Polymerization Example 1, but using 2.0 mg of the metallocene from Example 3.

This gives 25 g of polyethylene having a VN of 224 ml/g. GPC analysis indicates $M_w$=121400 g/mol and $M_w/M_n$=7.1.

We claim:

1. A catalyst component comprising a) at least one multinuclear metallocene compound of the formula I

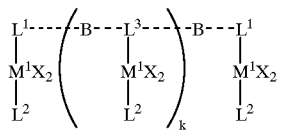

(I)

where $M^1$ is a tetravalent metal, $L^1$ are, independently of one another, identical or different and are each a substituted cyclopentadienyl group, $L^2$ and $L^3$ are, independently of one another, identical or different and are each a π-ligand, B are, independently of one another, identical or different and are each a divalent bridging unit, X are, independently of one another, identical or different and are each a hydrogen atom, a halogen atom, a $C_1$–$C_{10}$-fluorocarbon radical or a hydrocarbon-containing radical having 1–40 carbon atoms, and k is an integer from 0 to 10 and b) at least one cocatalyst selected from the group consisting of a boron compound and an aluminum alkyl.

2. A catalyst component as claimed in claim 1, wherein the catalyst component is in a supported form.

3. A catalyst component as claimed in claim 1, wherein the catalyst component is in a prepolymerized form.

4. The catalyst component as claimed in claim 3, wherein the prepolymerized catalyst component is also supported.

5. A catalyst component comprising at least one multinuclear metallocene compound of the formula I

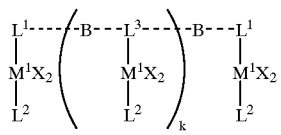

(I)

where $M^1$ is a tetravalent metal, $L^1$ are, independently of one another, identical or different and are each a substituted cyclopentadienyl group, $L^2$ and $L^3$ are, independently of one another, identical or different and are each a π-ligand, B are, independently of one another, identical or different and are each a divalent bridging unit, X are, independently of one another, identical or different and are each a hydrogen atom, a halogen atom, a $C_1$–$C_{10}$-fluorocarbon radical or a hydrocarbon-containing radical having 1–40 carbon atoms, and k is an integer from 0 to 10 with the proviso that $L^2$ is different from $L^1$ and b) at least one cocatalyst.

6. The catalyst component as claimed in claim 5, wherein the cocatalyst is an aluminum compound.

7. The catalyst component as claimed in claim 6, wherein the aluminum compound is aluminoxane and/or an aluminum alkyl.

8. The catalyst component as claimed in claim 5, wherein the cocatalyst is an aluminoxane of the formula VIIIa for the linear type and/or of the formula VIIIb for the cyclic type,

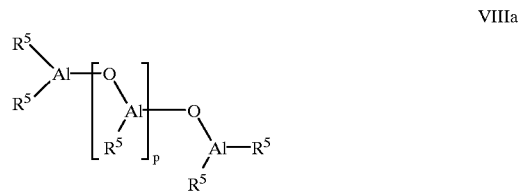

VIIIa

VIIIb where, in the formulae VIIIa and VIIIb, the radicals $R^5$ are identical or different and are each hydrogen or a $C_1$–$C_{18}$-alkyl group or a $C_6$–$C_{18}$-aryl group or a benzyl, and p is an integer from 2 to 50.

9. A catalyst component comprising at least one multinuclear metallocene compound of the formula I

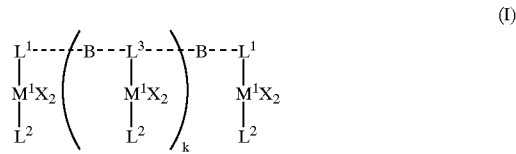

(I)

where $M^1$ is a tetravalent metal, $L^1$ are, independently of one another, identical or different and are each a substituted cyclopentadienyl group, $L^2$ is indenyl or a fluorenyl radical, $L^3$ is a π-ligand, B are, independently of one another, identical or different and are each a divalent bridging unit, X are, independently of one another, identical or different and are each a hydrogen atom, a halogen atom, a $C_1$–$C_{10}$-fluorocarbon radical or a hydrocarbon-containing radical having 1–40 carbon atoms, and k is an integer from 0 to 10 and b) at least one cocatalyst.

10. A catalyst component comprising a) at least one multinuclear metallocene compound of the formula I

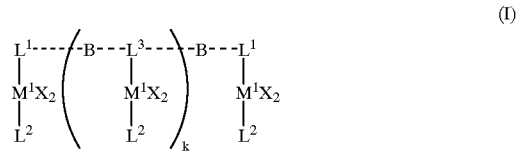

(I)

where $M^1$ is a tetravalent metal, $L^1$ are different and are each a substituted cyclopentadienyl group, $L^2$ and $L^3$ are, independently of one another, identical or different and are each a π-ligand, B are, independently of one another, identical or different and are each a divalent bridging unit, X are, independently of one another, identical or different and are each a hydrogen atom, a halogen atom, a $C_1$–$C_{10}$- fluorocarbon radical or a hydrocarbon-containing radical having 1–40 carbon atoms, and k is an integer from 0 to 10 and b) at least one cocatalyst.

* * * * *